US010822528B1

(12) United States Patent
Heshmati et al.

(10) Patent No.: US 10,822,528 B1
(45) Date of Patent: Nov. 3, 2020

(54) MULTI-LAYER POLYMER FORMULATIONS USED FOR SENSOR PROTECTION DURING DEVICE FABRICATION

(71) Applicant: Verily Life Sciences LLC, Mountain View, CA (US)

(72) Inventors: Parissa Heshmati, Oakland, CA (US); Jeffrey G. Linhardt, San Francisco, CA (US); Brian Alvarez, Oceanside, CA (US); Hojr Pisheh, Rohnert Park, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 303 days.

(21) Appl. No.: 16/115,359

(22) Filed: Aug. 28, 2018

Related U.S. Application Data

(60) Provisional application No. 62/551,073, filed on Aug. 28, 2017.

(51) Int. Cl.
| | | |
|---|---|---|
| *A61B 5/145* | (2006.01) | |
| *C09J 7/38* | (2018.01) | |
| *C09J 7/24* | (2018.01) | |
| *G01N 27/403* | (2006.01) | |

(Continued)

(52) U.S. Cl.
CPC ............. *C09J 7/38* (2018.01); *A61B 5/14532* (2013.01); *A61B 5/6821* (2013.01); *C09J 7/245* (2018.01); *G01N 27/403* (2013.01); *A61B 5/14552* (2013.01); *C09J 2203/326* (2013.01); *C09J 2301/502* (2020.08); *C09J 2400/20* (2013.01); *C09J 2471/00* (2013.01)

(58) Field of Classification Search
CPC .................. C09J 7/245; C09J 2301/502; C09J 2203/326; C09J 2400/20; C09J 2471/00; G01N 27/403; A61B 3/101; A61B 5/14532; A61B 5/1455; A61B 5/14552; A61B 5/1468; A61B 5/1477; A61B 5/6821; A61B 2562/12
See application file for complete search history.

(56) References Cited

U.S. PATENT DOCUMENTS

| | | |
|---|---|---|
| 8,922,366 B1 | 12/2014 | Honoré et al. |
| 9,128,305 B2 | 9/2015 | Honoré et al. |
| 9,307,901 B1 * | 4/2016 | Linhardt ................ A61B 3/101 |

(Continued)

OTHER PUBLICATIONS

US 8,884,753 B1, 11/2014, Honoré et al. (withdrawn)

*Primary Examiner* — Peter Dungba Vo
*Assistant Examiner* — Joshua D Anderson

(57) ABSTRACT

A protective layer for use on a sensor during a manufacturing process avoids damage to the sensor and keeps the sensor surface clean during lens fabrication. The protective layer includes a non-cross-linked, water-soluble polymer layer and an anhydrous, cross-linkable, methacrylate-based formulation layer, temporarily applied to a surface of the sensor. The protective layer may be used to protect the sensor during a manufacturing process by applying the non-cross-linked, water-soluble polymer layer and the anhydrous, cross-linkable, methacrylate-based formulation layer consecutively onto the surface of the sensor to form the protective layer; affixing the sensor to a substrate; fabricating a device that includes the substrate; and subsequently removing the protective layer from the surface of the sensor.

25 Claims, 7 Drawing Sheets

(51) Int. Cl.
 *A61B 5/00* (2006.01)
 *A61B 5/1455* (2006.01)

(56) References Cited

U.S. PATENT DOCUMENTS

| | | |
|---|---|---|
| 9,557,582 B2 | 1/2017 | Honoré et al. |
| 2009/0143761 A1 | 6/2009 | Cantor et al. |
| 2015/0004058 A1* | 1/2015 | Yao .................. G02C 11/10 422/68.1 |
| 2015/0005602 A1 | 1/2015 | Linhardt et al. |
| 2016/0066825 A1* | 3/2016 | Barrows .................. G02C 7/00 600/345 |
| 2016/0089068 A1 | 3/2016 | Simpson et al. |
| 2016/0242687 A1 | 8/2016 | Fujita et al. |
| 2016/0258964 A1 | 9/2016 | Zhang et al. |
| 2016/0332398 A1 | 11/2016 | Alli et al. |
| 2017/0074817 A1 | 3/2017 | Katase |

* cited by examiner

MULTI-LAYER POLYMER FORMULATIONS USED FOR SENSOR PROTECTION DURING DEVICE FABRICATION

BACKGROUND

When manufacturing a device that includes a sensor, such as a glucose-smart contact lens, the sensor surface requires full protection both to avoid damage and to keep the sensor surface clean during fabrication of the device. A protective layer can be applied to the sensor prior to initiating the fabrication of the device, and removed once the device has been formed. In order to successfully deposit and manipulate sensing chemistry on the manufactured glucose-smart contact lens, in particular, it is important to fully remove the protective layer from the sensor to achieve a pristine sensor surface.

When using a single-layer, cross-linked, polyethylene glycol (PEG) drop solution as the protective layer on a lens surface during lens fabrication, results showed evidence of residual PEG, silicone ingress, and unidentified contaminants after molding, indicating insufficient protection and a dirty sensor surface. Such residue on the sensor surface would interfere with enzyme chemistries subsequently applied to the sensor surface.

SUMMARY

A multi-layer protective layer can be applied to a surface of a sensor to protect the sensor during a manufacturing process in which the sensor is incorporated into a lens or other device. After the lens or other device has been fabricated, the protective layer is removed from the sensor to reveal a pristine sensor surface. The protection afforded by the protective layer prevents manufacturing residue from interfering with sensing chemistry that is subsequently applied to the sensor.

The protective layer may include a non-cross-linked, water-soluble, polymer layer and an anhydrous, cross-linkable, methacrylate-based formulation layer that is water swellable. More particularly, the protective layer may include a first layer of polyvinylpyrrolidinone, and a second layer that includes a cross-linkable polyethylene glycol. A method for protecting a sensor during a manufacturing process may include applying the protective layer to a surface of the sensor, affixing the sensor to a substrate, fabricating a lens or other device that includes the substrate, and subsequently removing the protective layer from the sensor.

BRIEF DESCRIPTION OF THE DRAWINGS

In order to describe the manner in which the above-recited and other advantages and features can be obtained, a more particular description is set forth and will be rendered by reference to specific examples thereof which are illustrated in the appended drawings. Understanding that these drawings depict only typical examples and are not therefore to be considered to be limiting of its scope, implementations will be described and explained with additional specificity and detail through the use of the accompanying drawings.

Figure 1A:
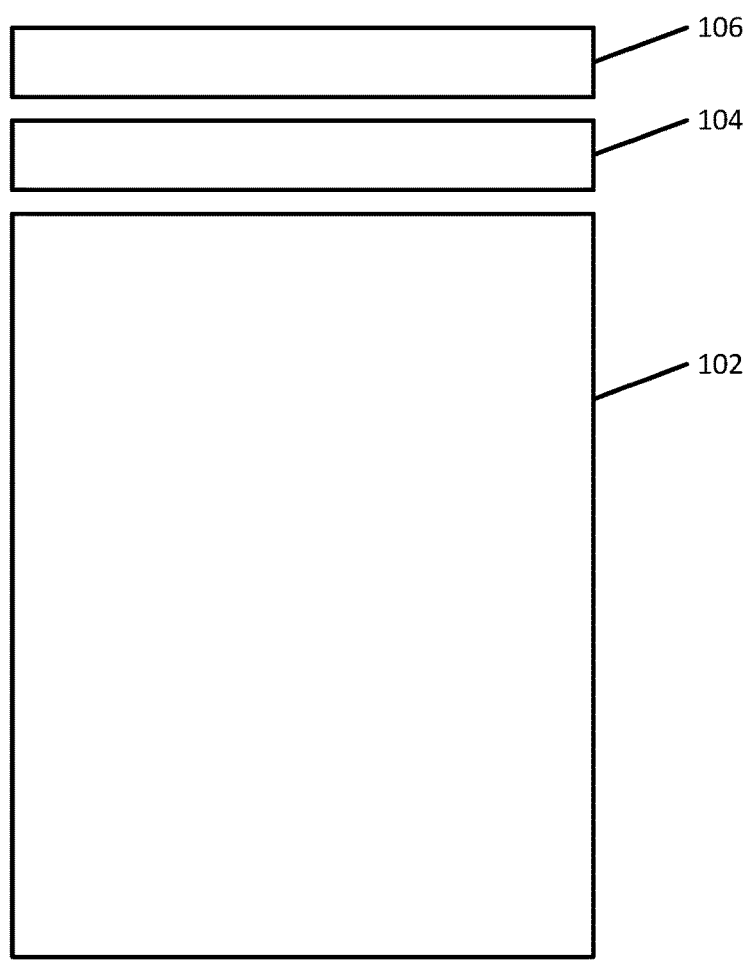
FIG. 1a depicts an exploded view of a sensor with a two-layer protective layer applied to a surface of the sensor, according to certain embodiments.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

An effective protective layer used for protecting a sensor during a manufacturing process must not only protect the sensor, but must also be removable from the sensor without leaving behind a residue. The multi-layer protective layer described herein is highly effective.

As shown in FIG. 1a, a surface of a sensor 102 can be protected during a manufacturing process by temporarily applying a multi-layer protective layer, illustrated as a two-layer protective layer 104 and 106 in this embodiment. The two-layer protective layer includes a non-cross-linked, water-soluble polymer layer 104 applied directly to a surface of the sensor 102, and an anhydrous, cross-linkable, methacrylate-based formulation layer 106 applied on top of the water-soluble polymer layer 104. Once the sensor 102 has been incorporated into a manufactured product, or at least partially-manufactured product, as explained in greater detail below, the protective layer 104, 106 can be removed from the sensor.

The water-soluble polymer layer 104 may include polyvinylpyrrolidinone (PVP), polyvinyl alcohol (PVA), polydimethylacrylamide (pDMA), or combinations thereof. PVP is a water-soluble polymer that can easily be applied and removed in fabrication processes. According to certain embodiments, the water-soluble polymer layer 104 may be about 1% to about 30%, or 3% to about 15% PVP solution in deionized water. For example, the water-soluble polymer layer 104 may be a 5% PVP solution in deionized water. The water-soluble polymer layer 104 can be dispensed onto the surface of the sensor 102 as a first protecting layer using a microcapillary injector.

The anhydrous, cross-linkable, methacrylate-based formulation layer 106 may include, for example, PEG475MA (polyethylene glycol methacrylate with an Mn of 475), PEG600DMA (polyethylene glycol dimethacrylate with an Mn of 600), 2-hydroxy-2-methylpropiophenone available from BASF under the trade name DAROCUR® 1173, or combinations thereof. In certain embodiments, the anhydrous methacrylate-based formulation layer 106 may include between about 50% and about 99%, or between about 80% and about 95% PEG475MA; between about 0.5% and about 50%, or between about 1% and about 20% PEG600DMA; and between about 0.1% and about 4%, or between about 1% and about 3% 2-hydroxy-2-methylpropiophenone.

The anhydrous, cross-linkable, methacrylate-based formulation layer 106 can be dispensed onto the surface of the sensor 102 atop the non-cross-linked, water-soluble polymer layer 104 as a second protecting layer also using a microcapillary injector, for example. After the sensor 102 has been incorporated into a final device, both layers 104 and 106 can be removed in water. This leads to an easier chemistry removal from the sensor surface, yielding a clean surface for further use. As a further benefit, this formulation does not contain any hazardous organic solvents, which makes it desirable for use in contact lenses and other devices that may be inserted into the body.

The application of an anhydrous, cross-linkable layer, such as the anhydrous methacrylate-based formulation layer 106, facilitates the formation of an open channel over the sensor surface. The anhydrous cross-linkable layer holds its shape after the cross-linking reaction.

Figure 1B:
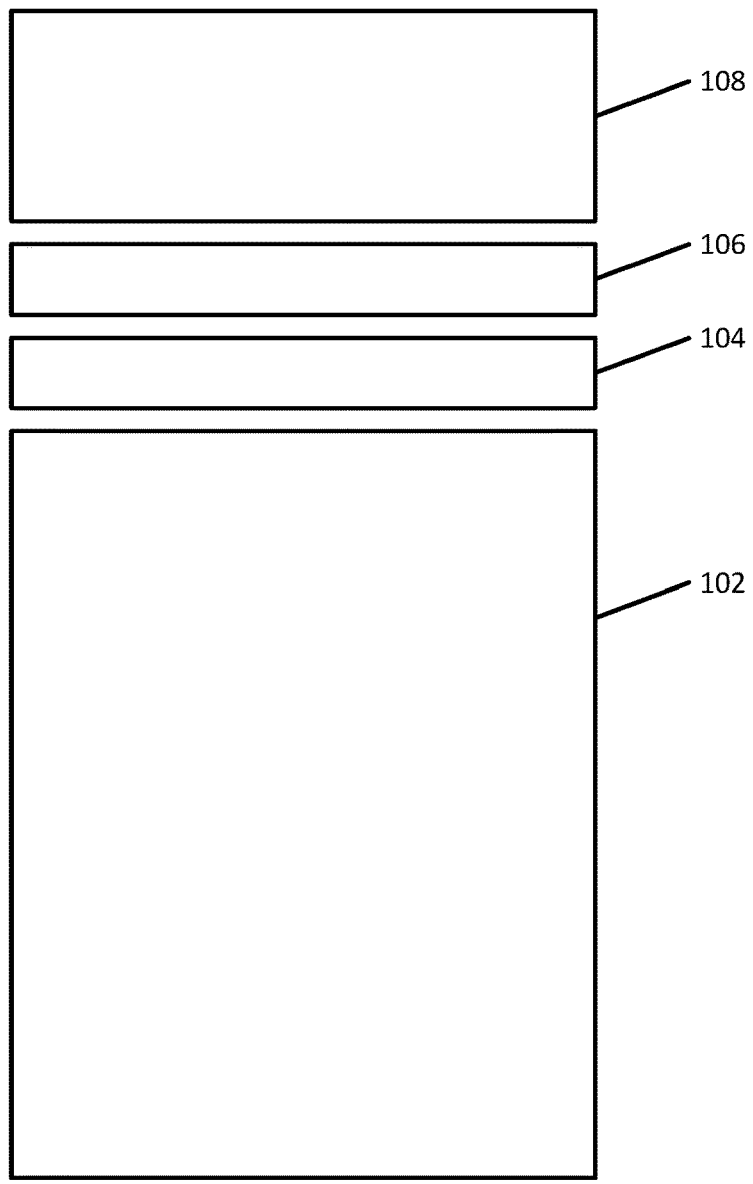
FIG. 1b depicts an exploded view of a sensor with a three-layer protective layer applied to a surface of the sensor, according to certain embodiments.

According to certain embodiments, the multi-layer protective layer may include more than two layers. For example, as shown in FIG. 1b, a polyethylene glycol (PEG) layer 108 may be applied atop the anhydrous, cross-linkable, methacrylate-based formulation layer 106 and the water-soluble polymer layer 104 as a third protecting layer, which is thereby coupled to the combined water-soluble polymer layer 104 and anhydrous, cross-linkable, methacrylate-based formulation layer 106, resulting in a single combined layer. The PEG layer 108 assists in removing the multi-layer protective layer from the surface of the sensor 102.

The overall protective layer 104 is formed from between about 1% to about 30%, or between about 3% and about 15% by weight non-cross-linked, water-soluble polymer layer 104; and between about 70% to about 99%, or between about 85% and about 97% by weight anhydrous methacrylate-based formulation layer 106.

Figure 2:
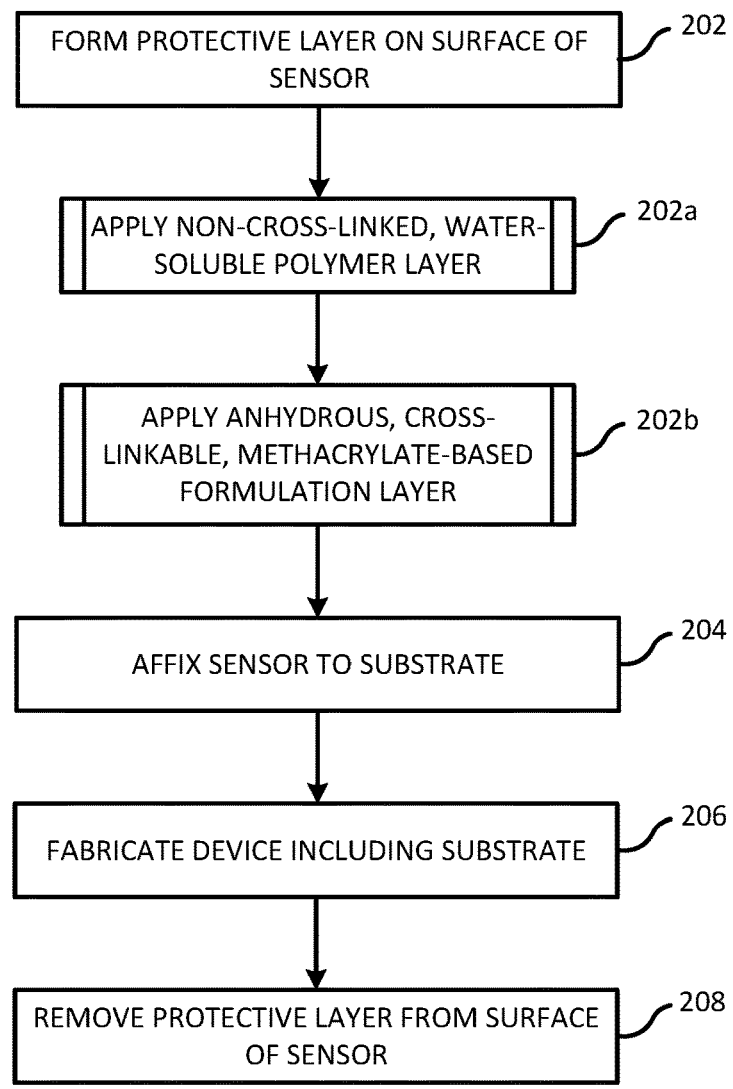
FIG. 2 is a flow diagram illustrating a method according to certain embodiments.

FIG. 2 is a flow chart illustrating a method 200 for protecting a sensor during a manufacturing process, according to an example embodiment. More specifically, the method 200 involves forming a protective layer on a surface of a sensor, as described above; namely, by first applying a water-soluble, non-crosslinked polymer layer, then applying an anhydrous, cross-linkable, methacrylate-based formulation layer on the surface of the sensor, as shown by block 202 and sub-blocks 202a and 202b. The method may then include affixing the sensor to a substrate, as shown by block 204. Further, the method may then include fabricating a device that includes the substrate, as shown by block 206. Next, the method may include removing the protective layer from the surface of the sensor, as shown by block 208. As explained below, the application of the protective layer need not be the first step, but instead may occur after the sensor has been affixed to the substrate, or even after fabrication of the device has begun.

A. Forming a Protective Layer on a Surface of a Sensor and Affixing the Sensor to a Substrate For purposes of illustration, the method 200 is described below as being carried out by a fabrication device that utilizes cast or compression molding, among other processes. It should be understood, however, that the method 200 may be carried out by a fabrication device that utilizes other methods and/or processes for forming body-mountable devices, such as injection molding or spin casting, for example.

Moreover, for purposes of illustration, the method 200 is described below in a scenario where a body-mountable device comprises an eye-mountable device. It should be understood, however, that the method 200 may involve scenarios where the body-mountable device comprises other mountable devices that are mounted on or in other portions of the human body. For example, the method 200 may involve a scenario where the body-mountable device comprises a tooth-mountable device and/or a skin mountable device.

Figure 3A:
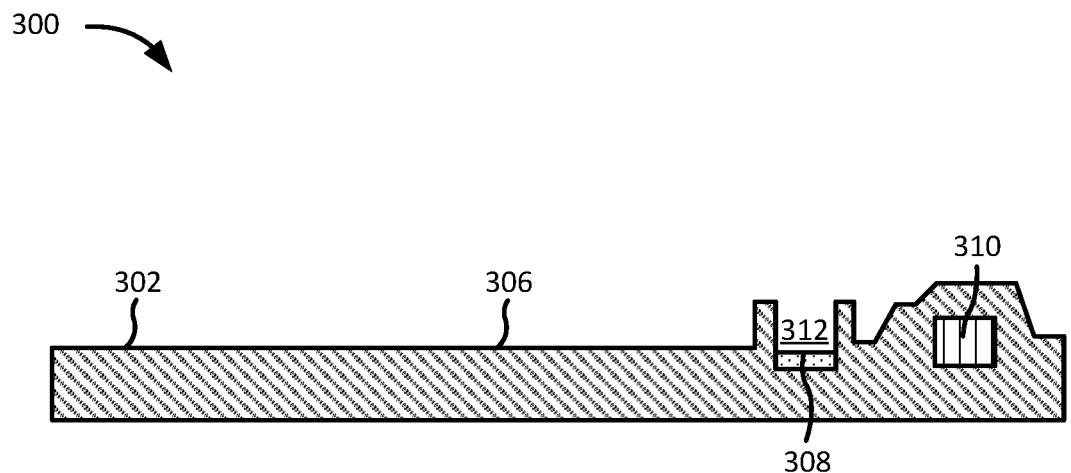
FIGS. 3a and 3b each depict equipment for forming a protective layer over a sensor, according to certain embodiments.
Figure 3B:
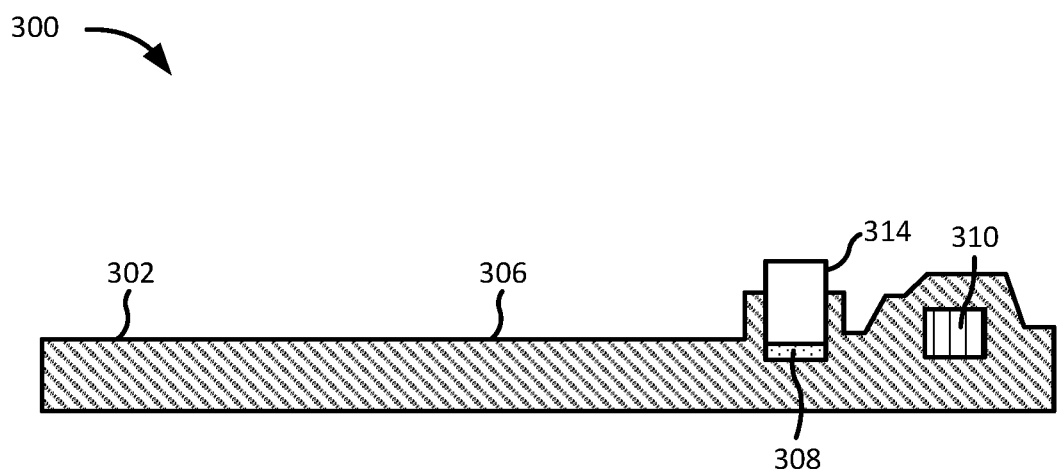

FIGS. 3a and 3b illustrate a fabrication device 300 that includes an example of equipment for forming a protective layer 314 over a sensor 308 located on a structure 302. In this example, the structure 302 includes a substrate 306, the sensor 308, and electronics 310. The structure 302 may occupy a peripheral portion of an eye-mountable device, such as an eye-mountable device 610 illustrated in FIGS. 6a and 6b, so as to limit interference with a user's field of view when the eye-mountable device is mounted on an eye of the user. The substrate 306 may comprise a variety of polymeric materials, such as parylene.

The sensor 308 may be applied to the substrate 306 prior to applying the protective layer 314 to the sensor 308. Alternatively, the protective layer 314 may be applied to the sensor 308 prior to applying the sensor 308 to the substrate 306. In the embodiment illustrated in FIGS. 3a and 3b, the sensor 308 is applied to the substrate 306 prior to applying the protective layer 314 to the sensor 308.

In the illustrated example, the electronics 310 are embedded in the substrate 306, and the sensor 308 is surrounded by the substrate 306, except for the sensor 308 being exposed by an opening 312, as shown in FIG. 3a. However, in other examples, the sensor 308 and electronics 310 may be mounted on a top surface of the substrate 306. In such an arrangement, the structure 302 might not include the opening 312. In some embodiments, the opening 312 can have a dimension of between 500 to 700 micrometers. Other dimensions are possible as well. And, in some embodiments, the opening 312 can have a square shape with rounded corners. Other shapes are possible as well, such as rectangular, circular, etc.

The structure 302 can have various sizes. For instance, the size of the structure 302, specifically the sensor 308 within the structure, may depend on which analyte (or analytes) an eye-mountable device is configured to detect. In an example, the structure 302 is a substrate shaped as a ring with approximately a 1 centimeter diameter, a radial thickness of approximately 1 millimeter, and a maximum height between approximately 50 and 150 micrometers. Of course, other sizes of the structure 302 are possible as well.

The sensor 308 can be configured in a variety of ways. As one example, the sensor 308 may comprise a pair of electrodes, such as a working electrode and a reference electrode, configured to detect one or more analytes. The sensor 308 may be an electrochemical sensor, for example. Other configurations of the sensor 308 are possible as well. The sensor 308 can have a variety of thicknesses. As one example, the sensor 308 can have a thickness of 260 nanometers. Other thicknesses of the sensor 308 are possible as well.

The electronics 310 can be configured in a variety of ways. As one example, the electronics 310 can comprise a chip including one or more logic elements configured to operate the sensor 308. Other configurations of the electronics 310 are possible as well.

In an example, forming the protective layer 314 over the sensor 308 located on the structure 302, as shown in FIG. 3b, can include injecting a non-cross-linked, water-soluble polymer layer, specifically a PVP layer, and an anhydrous, cross-linkable, methacrylate-based formulation layer over the sensor 308.

In some embodiments, the fabrication device 300 may include an injector, such as a microcapillary injector, that injects the PVP layer and the anhydrous, cross-linkable, methacrylate-based formulation layer over the sensor 308. With this approach, the injector can inject a predetermined quantity of each of the layers over the sensor 308. In such embodiments, the injector may be a NANOJECT™ sold by Debiotech.

B. Fabricating a Device that Includes the Substrate

Once the protective layer has been applied to the surface of the sensor and the sensor is affixed to a substrate, the sensor and substrate may then be fabricated into a device. For example, a body-mountable device may be configured to monitor health-related information based on at least one analyte detected in a fluid of a user wearing the body-mountable device. The body-mountable device may comprise an eye-mountable device that may be in the form of a contact lens that includes a sensor configured to detect the at least one analyte (e.g., glucose) in a tear film of a user wearing the eye-mountable device, also known as a glucose-smart contact lens. The multi-layer protective layer may also be used in the manufacturing processes of under lid devices, wired lenses, and any other lens variations. The body-mountable device may also be configured to monitor various other types of health-related information. More particularly, the protective layer may be used in the manufacture of implant devices or body-mountable devices in which a sensor comes into contact with blood, saliva, perspiration, interstitial fluid, or other bodily fluids that move into and out of the device.

Figure 4:
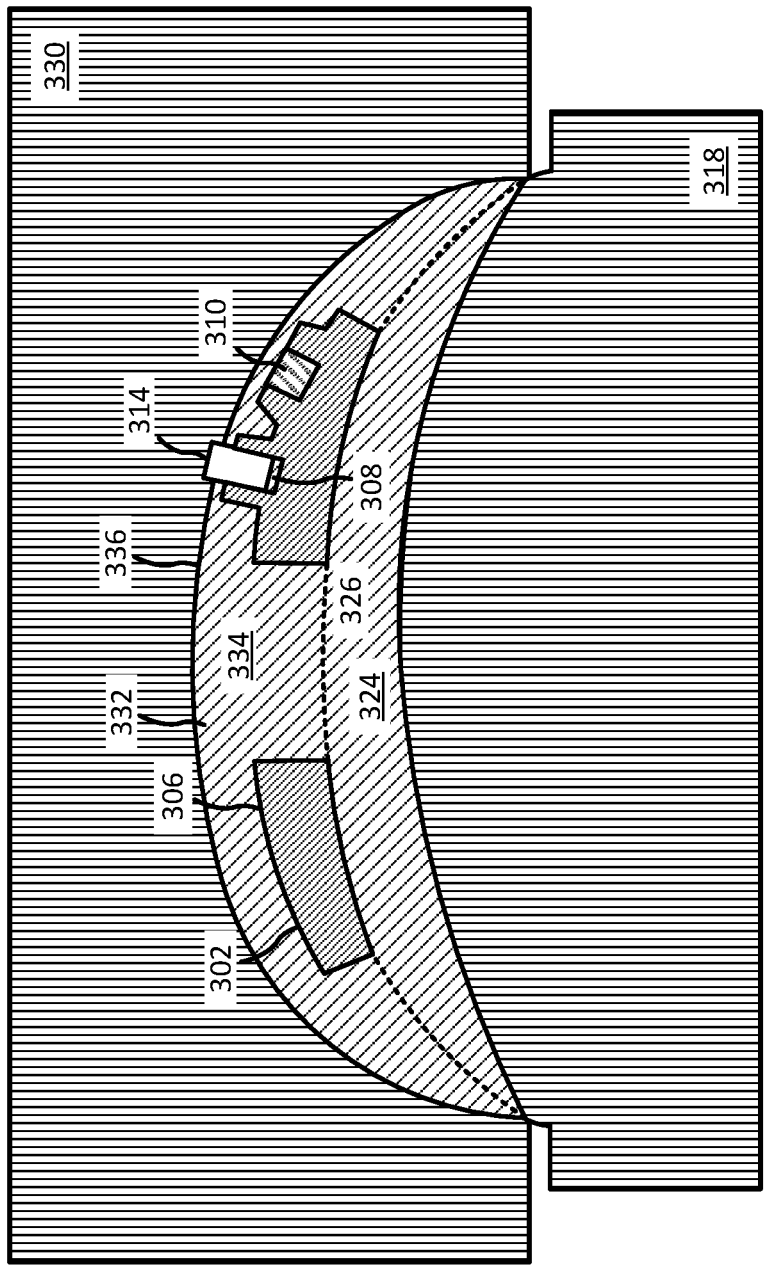
FIG. 4 depicts a sensor covered by a protective layer, located on a substrate and positioned between first and second polymer layers, according to certain embodiments.

FIG. 4 illustrates an example of additional equipment used in the fabrication device 300 illustrated in FIGS. 3a and 3b. The fabrication device 300 may include molding pieces, such as molding pieces that are suitable for cast molding a first polymer layer 324 onto which the substrate and sensor may be placed, and a second polymer layer 334 cast on top of the first polymer layer 324, the substrate and the sensor. In particular, FIG. 4 illustrates a first molding piece 318 and a second molding piece 330 that define a cavity for forming the first polymer layer 324 and the second polymer layer 334.

The polymer material 324, 334 can be any material that can form an eye-compatible polymer layer. For example, the polymer material 324, 334 may be a formulation containing polymerizable monomers, such as hydrogels, silicone hydrogels, silicone elastomers, and rigid gas permeable materials. Other materials are possible as well. The second polymer layer 334 can be composed of the same polymer material as the first polymer layer 324. Alternatively, the second polymer layer 334 can be composed of a different polymer material than the first polymer layer 324. Further, the polymer material 324, 334 may form a transparent or substantially transparent polymer layer. As such, the use of the polymer material 324, 334 may result in an eye-mountable device through which the wearer can see when mounted on the wearer's eye.

The first polymer layer 324 defines a posterior side 326 of an eye-mountable device. That is, the first polymer layer 324 defines an outer edge of the eye-mountable device. When mounted on an eye of a user, the posterior side 326 of the eye-mountable device defined by the first polymer layer 324 corresponds to a side of the device touching the eye of the user. The first molding piece 318 may be shaped so as to define a shape of the posterior side 326. For example, a curvature of the posterior side 326 may be defined by the first molding piece 318.

The first molding piece 318, which already holds the first polymer layer 324 to which the structure 302 is mounted, may be filled with a polymer material. The polymer material may be formed into a second polymer layer 334 by compression between the first molding piece 318 and the second molding piece 330. However, the protective layer 314 may block the second polymer layer 334 from molding over the sensor 308. As a result, the second polymer layer 334 may mold over the structure 302, such that the structure 302 is fully enclosed by the first polymer layer 324, the second polymer layer 334, and the protective layer 314. There may or may not be a visible boundary line separating the first polymer layer 324 from the second polymer layer 334.

The second polymer layer 334 defines an anterior side 336 of an eye-mountable device. That is, the second polymer layer 334 defines an outer edge of the eye-mountable device. When mounted on an eye of a user, the anterior side 336 of the eye-mountable device defined by the second polymer layer 334 corresponds to the side of the device that is not touching the eye of the user. The second molding piece 330 may be shaped so as to define a shape of the anterior side 336. For example, a curvature of the anterior side 336 may be defined by the second molding piece 330.

In an alternative embodiment, the protective layer 314 may be applied to the sensor 308 after the sensor 308 has been affixed to the substrate 306 and the substrate has been affixed to the first polymer layer 324, and prior to forming the second polymer layer 334 over the first polymer layer 324.

In another alternative embodiment, the first polymer layer 324 and the second polymer layer 334 may be formed around the structure 302 at the same time.

C. Removing the Protective Layer from the Surface of the Sensor

Figure 5A:
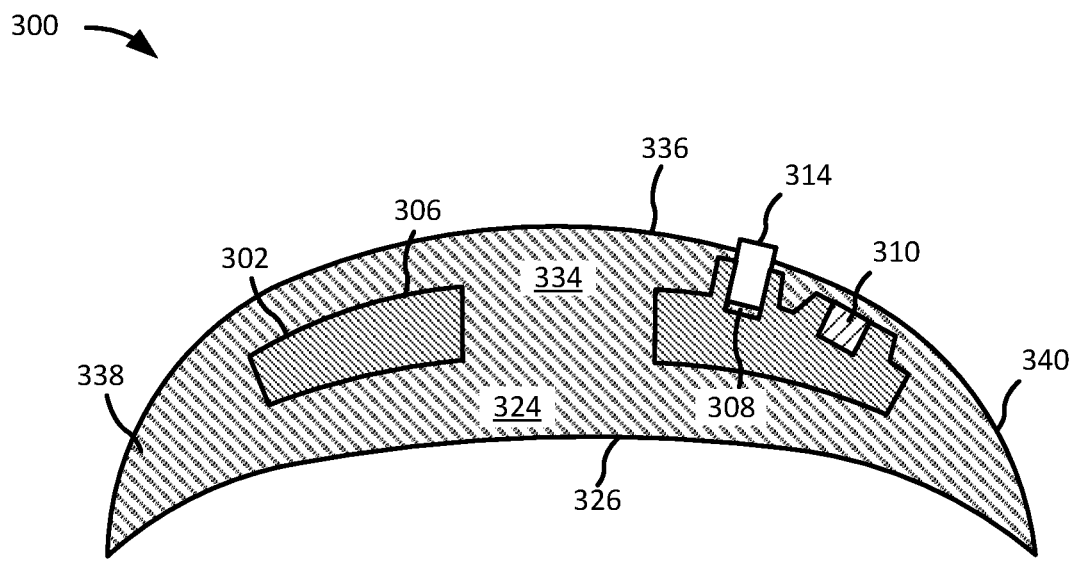
FIG. 5a depicts a partially-fabricated device soaking in a fluid, according to certain embodiments.

FIG. 5a illustrates a partially-fabricated device (or a device) 340. As shown in FIG. 5a, the partially-fabricated device 340 includes the structure 302, the sensor 308, the electronics 310, the protective layer 314, the posterior side 326, the anterior side 336, and a transparent polymer 338. The transparent polymer 338 includes the first polymer layer 324 and the second polymer layer 334.

Figure 5B:
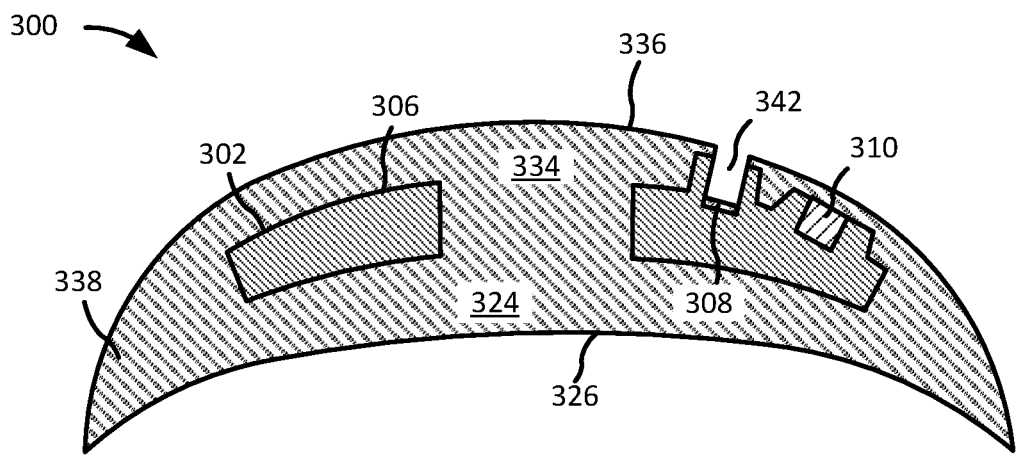
FIG. 5b depicts a partially-fabricated device with the protective layer removed from the sensor, according to certain embodiments.

One technique for removing the protective layer 314 from the surface of the sensor 308 within the fabricated or partially-fabricated device is to soak the device in a fluid, such that the protective layer swells out of the partially-fabricated device to leave a channel in the second polymer layer 334. FIG. 5a illustrates the fabrication device 300 at the outset of soaking the partially-fabricated device. FIG. 5b illustrates a later stage of soaking, in which the protective layer 314 swells out of the partially-fabricated device 340 to leave a channel 342 in the second polymer layer 334. In particular, the anhydrous, cross-linkable, methacrylate-based formulation layer and/or additional PEG layer is primarily responsible for the swelling of the protective layer, which can pull the entire protective layer 314 away from the sensor 308. Any water-soluble polymer remaining on the surface of the sensor 308 simply dissolves away.

The fluid can include one or more fluids selected from the group consisting of an aqueous solution and an organic solvent. The aqueous solution can be pure water, acidic, basic or buffered, such as phosphate buffered saline. The organic solvent can be a water-miscible solvent, such as tetrahyrofuran (THF), acetone or acetonitrile, a chlorinated solvent, such as dichloromethane or chloroform, or other solvent such as ethyl acetate or hexanes. In some embodiments, the fluid is a homogeneous mixture of an aqueous solution and an organic solvent, such as water/THF or water/acetonitrile.

In some instances, after the protective layer has been removed from the sensor, sensing chemistry can be deposited on the sensor. More particularly, a reagent can be included to sensitize the electrochemical sensor to desired analytes. For example, an enzymatic application, such as a layer of glucose oxidase (GOx), can be situated around the working electrode to catalyze glucose into hydrogen peroxide ($H_2O_2$). The hydrogen peroxide can then be oxidized at the working electrode, which releases electrons to the working electrode, which generates a current.

Figure 6A:
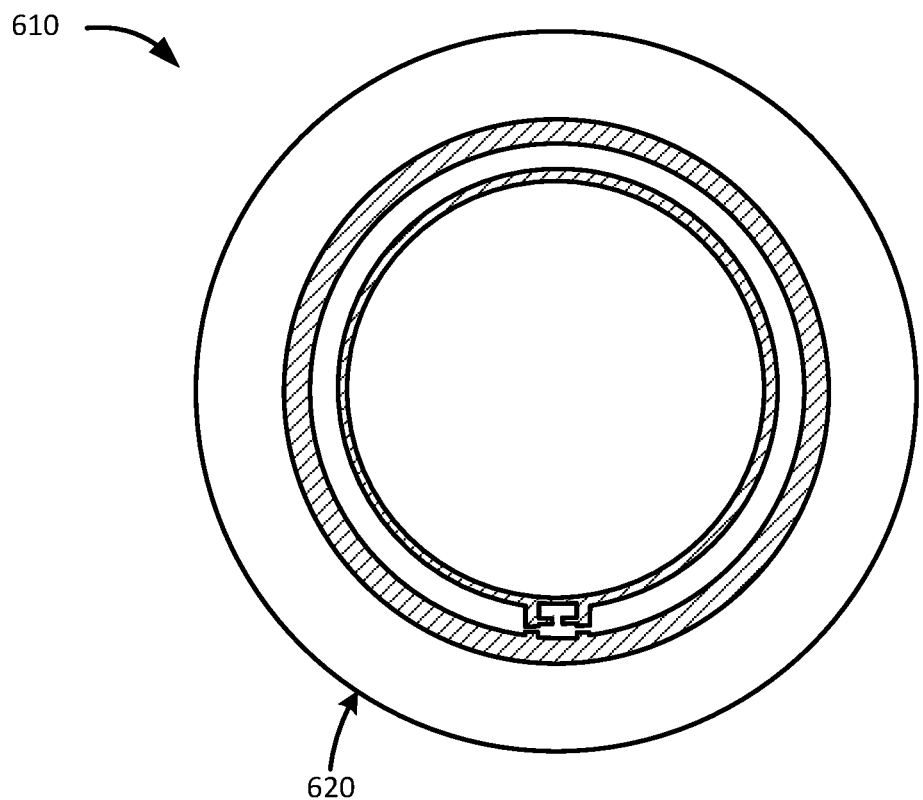
FIG. 6a is a top view of an eye-mountable device, according to certain embodiments.
Figure 6B:
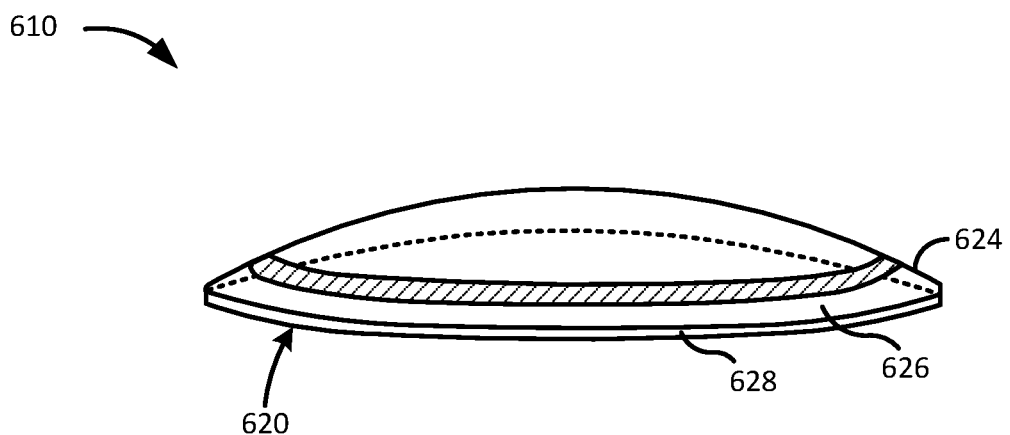
FIG. 6b is a side view of the eye-mountable device of FIG. 6a, according to certain embodiments.

FIG. 6a is a top view of an eye-mountable electronic device 610. FIG. 6b is a side view of the eye-mountable electronic device shown in FIG. 6a. It is noted that relative dimensions in FIGS. 6a and 6b are not necessarily to scale, but have been rendered for purposes of explanation only in describing the arrangement of the eye-mountable electronic device 610. The eye-mountable device 610 is formed of a polymeric material 620 shaped as a curved disk. The polymeric material 620 can be a substantially transparent material to allow incident light to be transmitted to the eye while the eye-mountable device 610 is mounted to the eye. The polymeric material 620 can be a biocompatible material similar to those employed to form vision correction and/or cosmetic contact lenses in optometry, such as polyethylene terephthalate (PET), polymethyl methacrylate (PMMA), silicone hydrogels, combinations of these, etc. The polymeric material 620 can be formed with one side having a concave surface 626 suitable to fit over a corneal surface of an eye. The opposing side of the disk can have a convex surface 624 that does not interfere with eyelid motion while the eye-mountable device 610 is mounted to the eye. A circular outer side edge 628 connects the concave surface 624 and convex surface 626.

While the eye-mountable device 610 is mounted in an eye, the convex surface 624 (i.e., the anterior surface) faces outward to the ambient environment while the concave surface 626 (i.e., the posterior surface) faces inward, toward the corneal surface. The convex surface 624 can therefore be considered an outer, top surface of the eye-mountable device 610 whereas the concave surface 626 can be considered an inner, bottom surface. The "top" view shown in FIG. 6a is facing the convex surface 624.

Comparative Examples

In the examples below, either a single-layer PEG drop solution was used as a protective layer on sensors (Examples 1-4), or a two-layer protective layer was used as a protective layer on sensors (Examples 5-14). The two-layer protective layer included a PVP layer or a PVA first layer and an anhydrous methacrylate-based formulation second layer as detailed in the tables below.

TABLE 1

Examples 1-7

| | Material | Example 1 | Example 2 | Example 3 | Example 4 | Example 5 | Example 6 | Example 7 |
|---|---|---|---|---|---|---|---|---|
| 1 | Water Soluble Polymer | — | — | — | — | 15% PVA(9K) 80% OH | 5% PVA(9.5K) 80% OH | 15% PVA(9K) 80% OH |
| 2 | PEG475MA | 62.5% | 97.5% | 95.6% | 72.4% | 98.5% | 62.3% | 78.3% |
| 2 | PEG600DMA | 35.5% | — | 2.4% | 25.6% | 1.0% | 34.7% | 18.7% |
| 2 | EGDMA | — | 0.5% | — | — | — | — | — |
| 2 | Darocur ® 1173 | 2.0% | 2.0% | 1.0% | 2.0% | 0.5% | 3.0% | 3.0% |

TABLE 2

Examples 8-14

| | Material | Example 8 | Example 9 | Example 10 | Example 11 | Example 12 | Example 13 | Example 14 |
|---|---|---|---|---|---|---|---|---|
| 1 | Water Soluble Polymer | 15% PVP(10k) | 5% PVP(10k) | 15% PVP(10k) | 5% PVP(10k) | 15% PVP(10k) | 5% PVP(10k) | 5% PVA(9.5K) 80% OH |
| 2 | PEG475MA | 89.4% | 95.6% | 62.3% | 72.4% | 91.4% | 84.5% | 98.5% |
| 2 | PEG600DMA | 7.6% | 2.4% | 34.7% | 25.6% | 7.6% | 14.5% | — |
| 2 | EGDMA | — | — | — | — | — | — | 0.5% |
| 2 | Darocur ® 1173 | 3.0% | 2.0% | 2.0% | 2.0% | 1.0% | 1.0% | 1.0% |

Table Key: In the tables above, the 1 or 2 in the left hand column refers to whether the material was used in the first layer or the second layer. — indicates that a material was not used in this layer. PVA(9K) = Poly(vinyl alcohol) $M_w$ 9,000-10,000, 80% hydrolyzed; PVP(10k) = Polyvinylpyrrolidone $M_w$ 10,000; PEG475MA = Poly(ethylene glycol) methacrylate $M_w$ 475; PEG600DMA = Poly(ethylene glycol) dimethacrylate $M_w$ 600; EGDMA = Ethylene glycol dimethacrylate; Darocur ® 1173 = 2-Hydroxy-2-methylpropiophenone For the example formulations above, ten sensors were treated with single-layer or two-layer protective layers and sent through a molding process. After the molding process the protective layers were removed from each sensor and analyzed for surface cleanliness.

Images of sensor surfaces showed evidence of residual PEG, silicone ingress, and unidentified contaminants after molding on the sensors protected with a single PEG layer, indicating insufficient protection and a dirty sensor surface. Further assessments using light microscopy imaging and FIB/SEM/EDS showed presence of PEG residue on the sensor surfaces of the sensors protected with a single PEG layer. The sensors that utilized the two-layer protective chemistry demonstrated a notable improvement in clean sensors that lacked surface contaminants (yield increased from ~30% to greater than 80%).

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

What is claimed is:

1. A multi-layer protective layer for use on a sensor during a lens manufacturing process, the multi-layer protective layer comprising:
    a non-cross-linked, water-soluble polymer layer applied to a surface of the sensor; and
    an anhydrous, cross-linkable, methacrylate-based formulation layer applied to a top surface of the non-cross-linked, water-soluble polymer layer;
    wherein the non-cross-linked, water-soluble polymer layer and the anhydrous, cross-linkable, methacrylate-based formulation layer are configured to be removed from the surface of the sensor by soaking the sensor in a fluid to form a channel to expose the surface of the sensor.

2. The multi-layer protective layer of claim 1, wherein the non-cross-linked, water-soluble polymer layer comprises 1% to 30% by volume polyvinylpyrrolidinone in de-ionized water.

3. The multi-layer protective layer of claim 1, wherein the anhydrous, cross-linkable, methacrylate-based formulation layer comprises a cross-linked polyethylene glycol.

4. The multi-layer protective layer of claim 1, wherein the anhydrous, cross-linkable, methacrylate-based formulation layer comprises PEG475MA, PEG600DMA, and 2-hydroxy-2-methylpropiophenone.

5. The multi-layer protective layer of claim 1, wherein the anhydrous, cross-linkable, methacrylate-based formulation layer comprises 50% to 99% by weight PEG475MA.

6. The multi-layer protective layer of claim 1, wherein the anhydrous, cross-linkable, methacrylate-based formulation layer comprises 0.5% to 50% by weight PEG600DMA.

7. The multi-layer protective layer of claim 1, wherein the anhydrous, cross-linkable, methacrylate-based formulation layer comprises 0.1% to 4% by weight 2-hydroxy-2-methylpropiophenone.

8. The multi-layer protective layer of claim 1, wherein the non-cross-linked, water-soluble polymer layer is in direct contact with the anhydrous, cross-linkable, methacrylate-based formulation layer.

9. The multi-layer protective layer of claim 1, further comprising a polyethylene glycol layer.

10. The multi-layer protective layer of claim 1, wherein the sensor is an electrochemical sensor.

11. A method from protecting a sensor during a lens manufacturing process comprising:
    applying a non-cross-linked, water-soluble polymer layer onto a surface of the sensor and applying an anhydrous, cross-linkable, methacrylate-based formulation layer onto a top surface of the non-cross-linked, water-soluble polymer layer to form a multi-layer protective layer;
    affixing the sensor to a substrate; and
    removing the multi-layer protective layer from the surface of the sensor, thereby forming a channel to expose the surface of the sensor.

12. The method of claim 11, further comprising applying a polyethyleneglycol layer onto a surface of the anhydrous, cross-linkable, methacrylate-based formulation layer after applying the anhydrous, cross-linkable, methacrylate-based formulation layer onto the top surface of the non-cross-linked, water-soluble polymer layer.

13. The method of claim 11, wherein the non-cross-linked, water-soluble polymer layer comprises 1% to 30% by volume polyvinylpyrrolidinone in de-ionized water.

14. The method of claim 11, wherein the anhydrous, cross-linkable, methacrylate-based formulation layer comprises PEG475MA, PEG600DMA, and 2-hydroxy-2-methylpropiophenone.

15. The method of claim 11, wherein the anhydrous, cross-linkable, methacrylate-based formulation layer comprises 50% to 99% by weight PEG475MA.

16. The method of claim 11, wherein the anhydrous, cross-linkable, methacrylate-based formulation layer comprises 0.5% to 50% by weight PEG600DMA.

17. The method of claim 11, wherein the anhydrous, cross-linkable, methacrylate-based formulation layer comprises 0.1% to 4% by weight 2-hydroxy-2-methylpropiophenone.

18. The method of claim 11, further comprising fabricating a device that includes the substrate after affixing the sensor to the substrate and before removing the multi-layer protective layer from the surface of the sensor.

19. The method of claim 11, further comprising depositing sensing chemistry onto the surface of the sensor after removing the multi-layer protective layer from the surface of the sensor.

20. The method of claim 19, wherein the sensing chemistry comprises an enzymatic application.

21. The method of claim 11, comprising affixing the sensor to a mounting surface of the substrate proximate a surface of a user's eye.

22. The method of claim 11, comprising affixing the sensor to a mounting surface of the substrate distal a surface of a user's eye.

23. The method of claim 11, wherein the sensor is an electrochemical sensor.

24. The method of claim 11, wherein the sensor is configured to obtain measurements related to glucose in tear film.

25. A method for protecting a sensor during a lens manufacturing process comprising:
- forming a multi-layer protective layer over the sensor by applying a non-cross-linked, water-soluble polymer layer on a surface of the sensor and applying an anhydrous, cross-linkable, methacrylate-based formulation layer onto a top surface of the non-cross-linked, water-soluble polymer layer, wherein the sensor is configured to detect an analyte;
- affixing the sensor to a substrate;
- forming a first polymer layer that defines a first side of an eye-mountable device;
- positioning the substrate on the first polymer layer;
- forming a second polymer layer over the first polymer layer and the substrate to provide a partially fabricated device in which the substrate is fully enclosed by the first polymer layer, the second polymer layer, and the multi-layer protective layer, wherein the second polymer layer defines a second side of the eye-mountable device; and
- soaking the partially-fabricated device in a fluid, such that the multi-layer protective layer swells out of the partially-fabricated device and is removed from the sensor, leaving a channel in the second polymer layer, wherein the sensor is configured to receive the analyte via the channel.

* * * * *

UNITED STATES PATENT AND TRADEMARK OFFICE
CERTIFICATE OF CORRECTION

PATENT NO. : 10,822,528 B1  
APPLICATION NO. : 16/115359  
DATED : November 3, 2020  
INVENTOR(S) : Parissa Heshmati et al.

Page 1 of 1

It is certified that error appears in the above-identified patent and that said Letters Patent is hereby corrected as shown below:

In the Claims

Column 10, Claim 11, Line 9, delete "from" and insert --for--

Column 10, Claim 12, Line 23, delete "polyethyleneglycol" and insert --polyethylene glycol--

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*